United States Patent [19]

Okumura et al.

[11] 4,243,657
[45] Jan. 6, 1981

[54] HAIR COSMETIC

[75] Inventors: Takeo Okumura, Sakura; Atsuo Ishida, Chiba; Shizuo Hayashi, Saitama, all of Japan

[73] Assignee: Kao Soap Co., Ltd., Tokyo, Japan

[21] Appl. No.: 938,838

[22] Filed: Sep. 1, 1978

Related U.S. Application Data

[63] Continuation of Ser. No. 730,350, Oct. 7, 1976, abandoned.

[30] Foreign Application Priority Data

Oct. 14, 1975 [JP] Japan ................................ 50-123392

[51] Int. Cl.$^3$ .......................... A61K 7/06; A61K 7/11
[52] U.S. Cl. .............................. 424/47; 424/DIG. 1; 424/DIG. 2; 424/70; 260/410.6
[58] Field of Search .................... 424/70, 47, DIG. 1, 424/DIG. 2, 71, 365; 260/410.6

[56] References Cited

U.S. PATENT DOCUMENTS

| | | | |
|---|---|---|---|
| 3,335,053 | 8/1967 | Weitzel | 260/410.6 X |
| 3,392,040 | 7/1968 | Kass | 424/70 X |
| 3,928,558 | 12/1975 | Cheesmen et al. | 424/47 |
| 3,972,914 | 8/1976 | Vanterburgh | 260/410.6 X |

FOREIGN PATENT DOCUMENTS

D. 14158 12/1956 Fed. Rep. of Germany .............. 424/70

*Primary Examiner*—Dale R. Ore
*Attorney, Agent, or Firm*—Blanchard, Flynn, Thiel, Boutell & Tanis

[57] ABSTRACT

A hair cosmetic composition comprising a cosmetic base containing 0.5 to 40% by weight of a diol derivative having the formula (I):

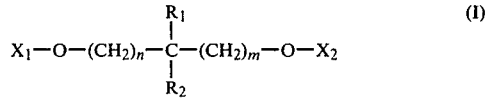

wherein $X_1$ is R—or

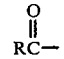

in which R is branched alkyl having 6 to 12 carbon atoms, $X_2$ is —H or

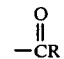

in which R is branched alkyl having 6 to 12 carbon atoms, $R_1$ is H, $CH_3$, $C_2H_5$ or $C_3H_7$, $R_2$ is H, $CH_3$, $C_2H_5$ or OH, and n and m each is an integer of from 1 to 3, or a branched aliphatic alcohol having the formula (II):

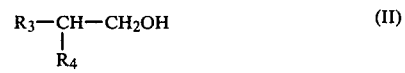

wherein $R_3$ is linear or branched alkyl having 8 to 10 carbon atoms and $R_4$ is linear or branched alkyl having 6 to 8 carbon atoms, said hair cosmetic composition also having incorporated therein from 0.5 to 10% of a methylpolysiloxane having the formula (III):

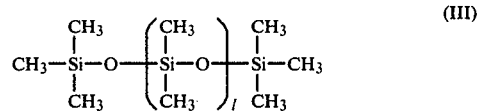

wherein l is an integer of from 3 to 14.

12 Claims, No Drawings

HAIR COSMETIC

BACKGROUND OF THE INVENTION

Field of the Invention

This is a continuation of application Ser. No. 730,350, filed Oct. 7, 1976, now abandoned.

The present invention relates to a cosmetic composition for protecting hair from mechanical stimuli.

Hair has a physiologically dead structure, and therefore if it is damaged, it cannot be restored to its original state. In general, when hair is damaged, lifting-up of cuticle scale edges or stripping-off of the scale surface occurs first and then, the hair is torn or split. The scales are a protective structure of hair, and lifting-up or stripping-off of the scales results in reduction of the resistance of hair to physical and chemical stimuli and promotes remarkably damage of hair. More specifically, various chemicals readily penetrate into the interior (hair cortex) of hair having damaged scales and natural moisturizing factors contained in hair are readily dissolved out. As a result, the hair readily becomes dry and loose. Furthermore, friction between individual hairs or between hair and a brush or comb is increased and the hair is further damaged as a result of mechanical effects.

It is considered that hair is damaged by chemical or physical treatments such as cold waving and hair brushing, and by ultraviolet rays and the like. Since the cystine content of the scale is high and the scale is brittle and brushing of hair is ordinarily conducted frequently, it is considered that the most important cause of damaged hair is the mechanical stimulus caused by brushing or the like.

Accordingly, it is important to protect hair from mechanical stimuli caused by brushing or the like in order to keep hair healthy, and a hair cosmetic having such effects is desired.

Hair creams and hair oils have heretofore been used as hair care products capable of meeting such requirements. However, the properties of the oil components incorporated into such hair cosmetics are not fully satisfactory for the reasons described below and various defects are caused after application thereof. In general, oil components used for hair creams, hair oils and the like have a high viscosity and their surface tension is higher than the critical surface tension of hair. Still further, since they have a high solidification point, they do not spread uniformly on the hair surface, but rather adhere locally thereon. Accordingly, after application, they make the hair heavy or sticky and the hair readily becomes dirty. At low temperatures, the treated hair becomes stiff or starchy. Moreover, because of the special forms of hair creams or hair oils, it is difficult to apply the oil components of these hair creams or hair oils uniformly to the entire hair surfaces, and a sufficient effect of protecting hairs from mechanical stimuli by reducing friction among hairs or between hair and a brush or comb cannot be obtained.

The present invention is intended to overcome the defects of conventional hair care products, and it is a primary object of the present invention to provide a hair cosmetic composition capable of better protecting hair from mechanical stimuli.

SUMMARY OF THE INVENTION

More specifically, in accordance with the present invention, there is provided a hair cosmetic composition comprising a cosmetic base containing (A) from 0.5 to 40 wt.%, preferably 2 to 20 wt.%, more preferably 5 to 15 wt.%, of a diol derivative having the formula (I):

$$X_1-O-(CH_2)_n-\underset{\underset{R_2}{|}}{\overset{\overset{R_1}{|}}{C}}-(CH_2)_m-O-X_2 \qquad (I)$$

wherein $X_1$ is -R or $$-R\overset{\overset{O}{\|}}{C}$$

in which R is branched alkyl having 6 to 12 carbon atoms, $X_2$ is -H or $$-\overset{\overset{O}{\|}}{C}R$$

in which R is branched alkyl having 6 to 12 carbon atoms, $R_1$ is H, $CH_3$, $C_2H_5$ or $C_3H_7$, $R_2$ is H, $CH_3$, $C_2H_5$ or OH, and n and m each is an integer of from 1 to 3, or a branched aliphatic alcohol having the formula (II):

$$R_3-\underset{\underset{R_4}{|}}{CH}-CH_2OH \qquad (II)$$

wherein $R_3$ is linear or branched alkyl having 8 to 10 carbon atoms and $R_4$ is linear or branched alkyl having 6 to 8 carbon atoms, said hair cosmetic composition also having incorporated therein, (B) from 0.5 to 10 wt.%, preferably 1 to 7 wt.%, more preferably 3 to 5 wt.%, of a methylpolysiloxane having the formula (III):

$$CH_3-\underset{\underset{CH_3}{|}}{\overset{\overset{CH_3}{|}}{Si}}-O\left(\underset{\underset{CH_3}{|}}{\overset{\overset{CH_3}{|}}{Si}}-O\right)_l\underset{\underset{CH_3}{|}}{\overset{\overset{CH_3}{|}}{Si}}-CH \qquad (III)$$

wherein $l$ is an integer of from 3 to 14, preferably 5 to 10.

In order to prevent damage of hair by mechanical stimuli caused by brushing or the like, it is necessary that the active components should spread uniformly on the hair surface and friction among hairs or between hair and a brush or comb should be reduced.

Therefore, an ideal component for protecting hair from mechanical stimuli is required, first of all, to have the property of reducing friction among hairs or between hair and a brush or comb.

Still in addition, since the temperature of hair is substantially equal to ambient temperature, the use of a component which is solid at ambient temperature is not preferred because it makes hair stiff or starchy after application and causes flaking when the hair is brushed. In other words, it is preferred that the active component be liquid at ambient temperature and that its solidification point be low.

If such a component has a high viscosity, it gives an unpleasant touch to hair after application and the hair becomes sticky. Accordingly, it is preferred that the viscosity of such a component be low even at low temperatures.

In short, it is desired that hair cosmetic compositions should have the following properties:
 (1) an excellent property of reducing friction among hairs or between hair and a brush or comb, namely, an excellent lubricating property;
 (2) spread uniformly on the hair surface;
 (3) a low solidification point and a low viscosity and the viscosity does not increase even at low temperatures;
 (4) reduced irritation of the scalp;
 (5) colorless and odorless; and
 (6) do not discolor or deteriorate with the passage of time.

Furthermore, when such a hair cosmetic composition is applied, it is necessary to spray it in the form of very fine particles and uniformly on the entirety of the hair. Water has bad effects on the hair setting or like hair manipulations after application. Thus, it has been confirmed that it is most preferred that the hair cosmetic be used in the form of an alcohol-based spray (aerosol or pump type). Therefore, it is necessary that the active component should be soluble in an alcohol and have a good compatibility with aerosol propellants, such as Freon propellants.

As a result of various research works and investigations made with a view to developing components satisfying all of the foregoing requirements, we discovered that the formula (I) diol derivative and the formula (II) branched aliphatic alcohol both are liquids having a low viscosity and a low solidification point and impart a good touch when applied to hair.

In general, a hair cosmetic composition is required to possess excellent finishing effects such as perfume and slipperiness. In this point, the formula (I) diol derivative is excellent but the formula (II) branched aliphatic alcohol is less satisfactory.

The formula (I) diol derivative or the formula (II) branched aliphatic alcohol is incorporated into a liquid cosmetic composition in an amount of 0.5 to 40 wt.%, preferably 2 to 20 wt.%, more preferably 5 to 15 wt.%. When the amount incorporated is less than 0.5 wt.%, the intended effects cannot be obtained at all, and when the amount incorporated is more than 40 wt.%, the viscosity of the resulting solution becomes too high.

However, it has been found that because the surface tension of such oil or fat (formula (I) or (II)) is higher than the critical surface tension of hair, it does not spread sufficiently on the hair surface. The critical surface tension of hair is hardly influenced by the relative humidity and it is about 26 to 27 dyne/cm at a relative humidity in the range of 20 to 90%. Accordingly, it is necessary to reduce the surface tension of the above component below the critical surface tension of hair.

It is impossible to reduce the surface tension of the above formula (I) or formula (II) oil or fat by adding a known non-ionic surface active agent, anionic surface active agent or cationic surface active agent. Rather, it is necessary to use a fluorine or silicone-type surface active agent. However, such surface active agents are expensive and are not readily available, and the use of such expensive surface active agents is not preferred for attaining the object of the present invention.

We discovered that the surface tension of the above formula (I) or formula (II) oil or fat can be effectively reduced by adding a low-molecular-weight methylpolysiloxane. In order to obtain a sufficient effect, the methylpolysiloxane must be incorporated in an amount of 0.5 to 10 wt.%, preferably 1 to 7 wt.%, more preferably 3 to 5 wt.%, based on the entire composition, and in an amount of from 1/10 to 8 times the weight of the above formula (I) or formula (II) oil or fat. It was found that the methylpolysiloxane not only has an effect of reducing the surface tension of the above formula (I) or formula (II) oil or fat, but also has an effect of reducing friction among hairs or between hair and a brush or comb. As a result of further investigations, it was found that the formula (III) methylpolysiloxane, in which l is from 3 to 14, preferably 5 to 10, is uniformly dissolved in an alcohol and reduces the surface tension of the above formula (I) or formula (II) oil or fat to below the critical surface tension of hair and that a mixture of this methylpolysiloxane with the above oil or fat spreads quickly on the hair surface as soon as it is applied thereto.

The solubility and surface tension reducing effect of the formula (III) methylpolysiloxane are illustrated in Tables 1 and 2. The solubility is the weight percentage of dissolved methylpolysiloxane in the total of the solvent and the methylpolysiloxane used.

TABLE 1

Solubilities of Methylpolysiloxanes (formula III) Differing in Degree of Polymerization, that is, Value of "l"

| Average degree (l + 2) of polymerization of methylpolysiloxane | 5 | 10 | 16 | 26 | 69 | 224 |
|---|---|---|---|---|---|---|
| | invention | | | controls | | |
| Viscosity (cps) of methylpolysiloxane | 2 | 5 | 10 | 20 | 100 | 1000 |
| Solvent, oil or fat | | | | | | |
| (1) Ethanol | o | o | o | Δ | X | X |
| (2) Propellant gas* | o | o | o | X | X | X |
| (3) 2-Octyldodecanol | | | Δ | X | X | X |
| (4) 2-Ethylhexyl glycerin | o | o | o | X | X | X |
| (5) 2-Methyl-2-propyl-1,3-propane-diol bis(2-ethylhexanoate) | o | o | o | Δ | X | X |

*monofluorotrichloromethane/difluorodichloromethane = 50/50
o : more than 40% dissolved
Δ : 10-40% dissolved
X : dissolved in amount less than 10%

TABLE 2

Surface Tension Reducing Effect of Formula III Methylpolysiloxane

| Weight Ratio | Surface Tension (dyne/cm) | Spreading on Hair |
|---|---|---|
| (1) 2-octyldodecanol: methylpolysiloxane (l + 2 = 10) | | |
| 100:0 | 36.1 | no spreading |
| 90:10 | 28.0 | slight spreading |
| 80:20 | 27.0 | spreading |
| 50:50 | 25.8 | quickly spreading |
| 30:70 | 24.5 | quickly spreading |
| 0:100 | 23.6 | quickly spreading |
| (2) 2-methyl-2-propyl-1,3-propane-diol bis(2-ethyl-hexanoate):methylpolysiloxane (l + 2 = 10) | | |
| 100:0 | 33.0 | no spreading |
| 90:10 | 29.0 | slight spreading |
| 80:20 | 26.5 | spreading |
| 50:50 | 25.3 | quickly spreading |
| 30:70 | 24.4 | quickly spreading |
| 0:100 | 23.6 | quickly spreading |

In general, the formula III methylpolysiloxanes in which the degree of polymerization (l+2) is from 69 to 420 and the viscosity is from 100 to 5000 cps are used in cosmetics. However, as illustrated in Table 1, the formula (III) methylpolysiloxane that is used in the present invention preferably has a polymerization degree (1+2) of 5 to 16 and a viscosity of 2 to 10 cps. If the degree of polymerization is higher than the above range, the compatibility thereof with the above formula (I) or formula (II) oil or fat is low and the surface tension reducing effect is insufficient. Further, a formula (III) methylpolysiloxane having a higher polymerization degree is insoluble in alcohols or propellant, such as Freon, and hence, an aerosol cosmetic of the alcohol-based type cannot be obtained. If the polymerization degree is lower then the above range, the methylpolysiloxane has a bad smell and possesses an insufficient lubricating effect and surface tension reducing effect.

Methylpolysiloxanes represented by the formula (III) can be prepared from organochlorosilanes such as methylchlorodisilane by (1) the direct method, (2) the Grignard method, (3) the olefin addition method and (4) other known method. In the present invention, a product prepared by any of these methods can be used.

Examples of the diol derivative of the formula (I) used in the present invention are as follows:

(1) 2-ethylhexylglyceryl ether 2,2-dimethyloctanoate $$C_4H_9-CH-CH_2-O-CH_2-CH-CH_2-OC-C-(CH_2)_5-CH_3$$
with $C_2H_5$, $OH$, $\overset{O}{\|}$, $CH_3$, $CH_3$ substituents (2) 2,2-dimethyl-1,3-propane-diol mono-2-ethylhexanoate $$C_4H_9-CH-CO-CH_2-C(CH_3)_2-CH_2-OH$$
with $C_2H_5$, $O$ substituents (3) 2,2-dimethyl-1,3-propane-diol bis(2-ethylhexanoate)

$$C_4H_9-CH-CO-CH_2-C(CH_3)_2-CH_2-OC-CH-C_4H_9$$
with $C_2H_5$, $O$, $O$, $C_2H_5$ substituents (4) 3-methylpentane-1,3,5-triol mono-2-ethylhexanoate $$C_4H_9-CH-CO-(CH_2)_2-C(CH_3)(OH)-(CH_2)_2-OH$$
with $C_2H_5$, $O$ substituents (5) 3-methylpentane-1,3,5-triol bis(2-ethylhexanoate)

$$C_4H_9-CH-CO-(CH_2)_2-C(CH_3)(OH)-(CH_2)_2-OC-CH-C_4H_9$$
with $C_2H_5$, $O$, $O$, $C_2H_5$ substituents (6) 2-methyl-2-propyl-1,3-propane-diol bis(2-ethylhexanoate)

$$C_4H_9-CH-CO-CH_2-C(CH_3)(C_3H_7)-CH_2OC-CH-C_4H_9$$
with $C_2H_5$, $O$, $O$, $C_2H_5$ substituents (7) 1,6-hexanediol bis(2,2-dimethyloctanoate)

$$C_6H_{13}-C(CH_3)_2-CO(CH_2)_6OC-C(CH_3)_2-C_6H_{13}$$
with $O$, $O$ substituents (8) 2-ethylhexylglyceryl ether 2-ethylhexanoate $$C_4H_9-CH-CH_2OCH_2CH-CH_2OCOCH-C_4H_9$$
with $C_2H_5$, $OH$, $C_2H_5$ substituents Each of the foregoing diol derivatives 1–8 has a solidification point lower than $-20°$ C. and a viscosity lower than 100 cps, and is homogeneously dissolved in an alcohol and propellant (Freon). Accordingly, they are suitable for use in the present invention.

These diol derivatives are prepared from glycols by a method using a halide of a saturated branched fatty acid, an esterification method utilizing an ester exchange reaction or an etherification method using an alkyl halide.

The formula (II) branched aliphatic alcohol of the following formula, that is used in the present invention, must have a saturated alkyl group:

$$R_3-CH-CH_2OH \quad (II)$$
$$|$$
$$R_4$$

wherein $R_3$ is a linear or branched alkyl group having 8 to 10 carbon atoms and $R_4$ is a linear or branched alkyl group having 6 to 8 carbon atoms.

These alcohols prepared according to the Gölbe reaction, the aldol condensation and the like method can be used in the present invention.

It is necessary that the formula (I) and formula (II) compound should have a solidification point lower than $-20°$ C. Use of an alcohol of the above formula (II) in which the total carbon atom number is smaller than 16 is not preferred because the alcohol irritates the skin and has a bad odor. Further, the use of an alcohol of the above formula (II) in which the total carbon atom number exceeds 20 is not preferred because flaking readily occurs during brushing. Examples of the alcohol of the above formula (II) used in the present invention are 2-hexyldecanol, 2-heptyldecanol, 2-octyldecanol, 2-hexylundecanol, 2-heptylundecanol, 2-octylundecanol, 2-hexyldodecanol, 2-heptyldodecanol and 2-octyldodecanol. A linear aliphatic alcohol cannot be used in the present invention because flaking readily occurs if it is used.

The hair cosmetic composition of the present invention can be employed in the form of a liquid cosmetic prepared by dissolving the foregoing components in a suitable solvent or the in form of an aerosol composition including a propellant gas.

The solvent that is used for preparation of a liquid cosmetic must quickly evaporate after it is applied to hair, have a good smell and be free of toxicity. For example, ethanol, propanol and isopropanol are preferably employed.

The solvent is used in such an amount that the diol derivative, the branched alcohol and the methylpolysiloxane are homogeneously dissolved therein. In general, the amount of the solvent is 50 to 95 wt.% based on the total weight of the solution.

An aerosol type cosmetic is prepared by packaging a propellant and the above-mentioned liquid cosmetic in an aerosol container in the conventional way.

As the propellant, there can be mentioned, for example, monofluorotrichloromethane, difluorodichloromethane, dichlorotetrafluoroethane, carbon dioxide gas and methane.

The propellant can be used in an amount of from ½ to 10 times the weight of the liquid cosmetic.

The present invention will now be described in detail by reference to the following illustrative examples, in which all references to "parts" mean parts by weight.

EXAMPLE 1

| | | |
|---|---|---|
| (1) | 2-Ethylhexylglyceryl ether 2-ethylhexanoate | 10 parts |
| (2) | 2-Hexyldecanol | 2 parts |
| (3) | Dimethylsiloxane (1 + 2 = 16) | 3 parts |
| (4) | Ethanol | 85 parts |
| (5) | Perfume | small amount |
| | Total | 100 parts |

The components (1), (2), (3) and (5) were homogeneously dissolved in ethanol to obtain a liquid hair cosmetic.

EXAMPLE 2

| | | |
|---|---|---|
| (1) | 2-Ethylhexylglyceryl ether 2,2-dimethyloctanoate | 10 parts |
| (2) | Methylpolysiloxane (1 + 2 = 5) | 4 parts |
| (3) | Anhydrous ethanol | 86 parts |
| (4) | Perfume | small amount |
| | Total | 100 parts |
| (5) | Monofluorotrichloromethane | same as amount of above solution (components 1 to 4) |
| (6) | Difluorodichloromethane | same as amount of above solution (components 1 to 4) |

The components other than the propellants (5) and (6) were mixed homogeneously to form a solution, and the solution was filled into an aerosol vessel. According to a conventional method, the propellants were charged into the aerosol vessel to obtain an aerosol type hair cosmetic.

EXAMPLE 3

| | | |
|---|---|---|
| (1) | 3-Methylpentane-1,3,5-triol bis(2-ethylhexanoate) | 5 parts |
| (2) | 2-Octyldodecanol | 2 parts |
| (3) | Methylpolysiloxane (1 + 2 = 10) | 5 parts |
| (4) | Anhydrous ethanol | 88 parts |
| (5) | Perfume | small amount |
| | Total | 100 parts |
| (6) | Difluorodichloromethane | same as amount of above solution of components 1 to 5 |
| (7) | Monofluorotrichloromethane | two times amount of above solution of components 1 to 5 |

An aerosol type hair cosmetic was prepared from the above components in the same manner as described in Example 2.

EXAMPLE 4

The hair cosmetic compositions prepared in Example 2 and 3 were respectively sprayed for 2 seconds onto 2 g of a bundle of hair, and the force applied to the hair when a plastic comb was drawn through the hair bundle was measured by using a Tensilon tensile tester (manufactured by Toyo Seiki). The results shown in Table 3 were obtained.

TABLE 3

| Treatment | Force Applied to Hair |
|---|---|
| commercial shampoo alone was used | 220 g |
| cosmetic composition of Example 2 was used after commercial shampoo had been used | 19 g |
| cosmetic composition of Example 3 was used after commercial shampoo had been used | 15 g |

From the above results, it is seen that when the cosmetic composition of the present invention is used for the hair treatment, the force applied to hair is reduced to about 1/10 of the force applied to hair when a commercial shampoo alone is used. Thus, it is expected that damages of hair caused by brushing will be greatly reduced by the use of the cosmetic composition of the present invention.

EXAMPLE 5

A bundle of 2000 women hairs which had not been subjected to a chemical treatment such as a cold waving treatment and which were scarcely damaged, was washed with a commercial shampoo and dried, and the hair bundle was brushed repeatedly by using a nylon brush. The number of split ends formed by the brushing was measured. The brushing was repeated 100 times after every time the hair bundle was washed with the shampoo. Similar tests were performed wherein the compositions of Examples 2 and 3 were respectively applied to the hair after it was shampooed and dried. The results are shown in Table 4. For comparison purposes, the results obtained when a commercial rinse was employed are also shown in Table 4.

TABLE 4

Number of Split Ends and Broken Hairs Caused by Brushing

| | Frequency of Brushing | | | |
|---|---|---|---|---|
| Treatment | 1000 times | 1500 times | 2000 times | 2500 times |
| commercial shampoo alone was used | 33 | 55 | 90 | 130 |
| commercial shampoo and commercial rinse were used | 25 | 39 | 59 | 90 |
| commercial shampoo and cosmetic of Example 2 were used | 3 | 5 | 8 | 13 |
| commercial shampoo and cosmetic of Example 2 were used | 2 | 2 | 3 | 5 |

When a commercial shampoo alone was used, a large number of split ends was formed. When a commercial rinse was used in combination with the commercial shampoo considerable numbers of split ends were formed. In contrast, when the compositions of Example 2 or 3 of the present invention were employed, the number of split ends formed by brushing was reduced to approximately 1/10.

From these experimental results, it is apparent that the hair cosmetic composition of the present invention has a remarkably improved effect of protecting hairs from mechanical stimuli caused by brushing or the like.

The embodiments of the invention in which an exclusive property or privilege is claimed are defined as follows:

1. A homogeneous liquid hair cosmetic composition consisting essentially of
A. from 0.5 to 40 weight percent of a substance having a solidification temperature lower than minus 20° C. and selected from the group consisting of
1. a compound having the formula

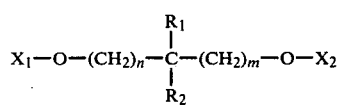

wherein $X_1$ is R- or

and $X_2$ is

or H, in which R is branched alkyl having 6 to 12 carbon atoms, $R_1$ is H, $CH_3$, $C_2H_5$ or $C_3H_7$, $R_2$ is H, $CH_3$, $C_2H_5$ or OH, and n and m each is an integer of from one to 3, and mixtures thereof, 2. a compound having the formula

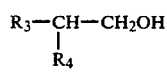

wherein $R_3$ is a linear or branched alkyl having 8 to 10 carbon atoms and $R_4$ is a linear or branched alkyl having 6 to 8 carbon atoms, and mixtures thereof, and 3. mixtures of component (1) and component (2), B. from 0.5 to 10 weight percent of a compound or mixture of compounds having the formula

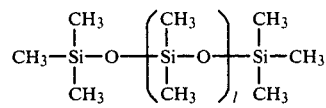

wherein l is an integer of from 3 to 14 and the viscosity of component B is from 2 to 10 cps, the weight ratio of components B/A being in the range of from 1/10 to 8/1, C. and the balance consists essentially of an alcohol solvent effective for dissolving components A and B and selected from the group consisting of ethanol, propanol and isopropanol.

2. A composition according to claim 1, containing from 2 to 20 weight percent of component A and from one to 7 weight percent of component B.

3. A composition according to claim 1, containing from 5 to 15 weight percent of component A and from 3 to 5 weight percent of component B.

4. A composition according to claim 1 wherein l is an integer of from 5 to 10.

5. A composition according to claim 1 in which component A is selected from the group consisting of 2-ethylhexylglyceryl ether 2,2-dimethyloctanoate, 2,2-dimethyl-1,3-propane-diol mono-2-ethylhexanoate, 2,2-dimethyl-1,3-propane-diol bis(2-ethylhexanoate), 3-methylpentane-1,3,5-triol mono-2-ethylhexanoate, 3-methylpentane-1,3,5-triol bis(2-ethylhexanoate), 2-methyl-2-propyl-1,3-propane-diol bis(2-ethylhexanoate), 1,6-hexanediol bis(2,2-dimethyloctanoate) and 2-ethylhexylglyceryl ether 2-ethylhexanoate.

6. A composition according to claim 1 in which component A is selected from the group consisting of 2-hexyldecanol, 2-heptyldecanol, 2-octyldecanol, 2-hexylundecanol, 2-heptylundecanol, 2-octylundecanol, 2-hexyldodecanol, 2-heptyldodecanol and 2-octyldodecanol.

7. A composition according to claim 1 in which the amount of component C is from 50 to 95 weight percent, based on the total weight of the composition.

8. A composition according to claim 1 packaged in a pressurized aerosol container in association with a propellant.

9. A composition according to claim 8 in which the amount of the propellant is from ½ to 10 times the sum of the weights of components A, B and C.

10. A composition as claimed in claim 1 in which component A consists of component A(1.).

11. A composition as claimed in claim 1 in which component A consists of component A(2.).

12. A composition as claimed in claim 1 in which component A consists of a mixture of component A(1) and component A(2).

* * * * *